United States Patent
Ottens

(10) Patent No.: US 10,085,817 B2
(45) Date of Patent: Oct. 2, 2018

(54) CONNECTING DEVICE, CLEANING AND/OR DISINFECTING DEVICE AND METHOD FOR THE OPERATION THEREOF

(71) Applicant: OLYMPUS WINTER & IBE GMBH, Hamburg (DE)

(72) Inventor: Benjamin Ottens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 118 days.

(21) Appl. No.: 15/274,807

(22) Filed: Sep. 23, 2016

(65) Prior Publication Data

US 2017/0007357 A1 Jan. 12, 2017

Related U.S. Application Data

(63) Continuation of application No. PCT/EP2015/055692, filed on Mar. 18, 2015.

(30) Foreign Application Priority Data

Mar. 31, 2014 (DE) ........................ 10 2014 206 020

(51) Int. Cl.
*A61B 90/70* (2016.01)
*A61B 1/00* (2006.01)
(Continued)

(52) U.S. Cl.
CPC .......... *A61B 90/70* (2016.02); *A61B 1/00128* (2013.01); *A61B 1/125* (2013.01);
(Continued)

(58) Field of Classification Search
None
See application file for complete search history.

(56) References Cited

U.S. PATENT DOCUMENTS

| | | |
|---|---|---|
| 4,042,248 A | 8/1977 | Williamitis |
| 5,083,802 A | 1/1992 | Shimasaki et al. |
| 5,931,647 A | 8/1999 | Jacobsen et al. |

FOREIGN PATENT DOCUMENTS

| | | |
|---|---|---|
| DE | 37 37 121 A1 | 5/1989 |
| EP | 2 098 185 A1 | 1/2009 |
| JP | 2004-135946 A | 5/2004 |

OTHER PUBLICATIONS

International Search Report dated Jun. 22, 2015 issued in PCT/EP2015/055692.

*Primary Examiner* — Eric W Golightly
(74) *Attorney, Agent, or Firm* — Scully, Scott, Murphy & Presser, P.C.

(57) ABSTRACT

A connecting device for coupling a rinsing system to a channel of a surgical instrument to be cleaned, including: a connecting element; a supply-side coupling apparatus having a holding channel to receive the connecting element extending within the holding channel in a longitudinal axial direction in a connected state, and which is provided at the end of a connecting channel that communicates with the channel, wherein the holding channel is connected to the rinsing system for feeding a rinsing liquid to the channel, wherein the coupling apparatus comprises a sealing element; and means for hydraulically and/or pneumatically actuating the sealing element; wherein the sealing element is elastic; and the sealing element reduces a cross-section of the holding channel in a region of the sealing element by means of an expansion transverse to the longitudinal axial direction) to provide a liquid-tight connection of the connecting element to the coupling apparatus.

10 Claims, 3 Drawing Sheets

(51) Int. Cl.
*A61B 1/12* (2006.01)
*A61L 2/00* (2006.01)
*F16J 15/32* (2016.01)
*A61L 2/18* (2006.01)
*B08B 3/04* (2006.01)
*F16L 37/62* (2006.01)
*A61B 17/00* (2006.01)

(52) U.S. Cl.
CPC .................... *A61L 2/00* (2013.01); *A61L 2/18* (2013.01); *B08B 3/04* (2013.01); *F16J 15/32* (2013.01); *F16L 37/62* (2013.01); *A61B 2017/00477* (2013.01); *A61B 2017/00544* (2013.01); *A61B 2090/701* (2016.02); *A61L 2202/24* (2013.01)

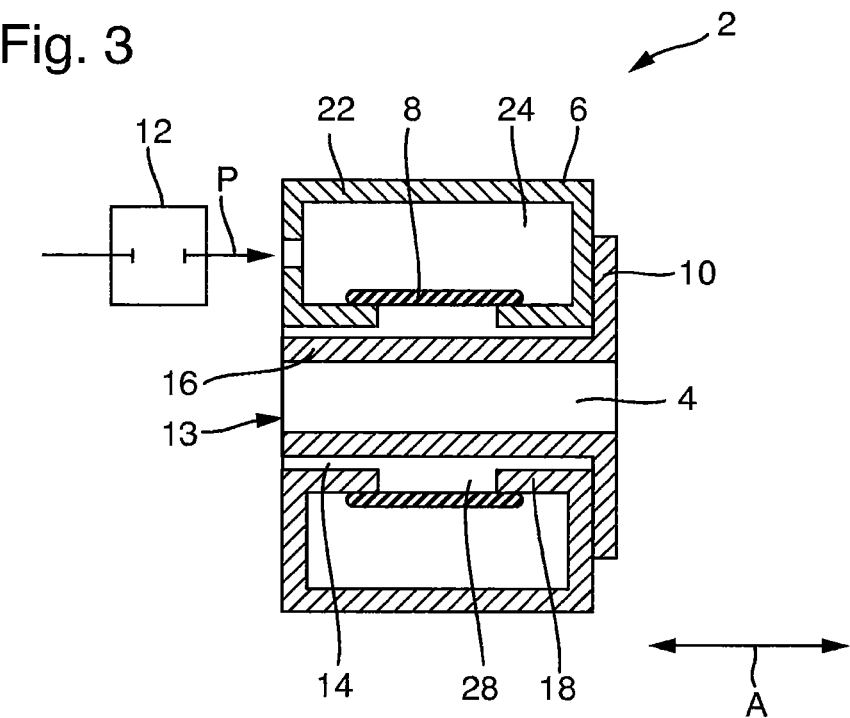
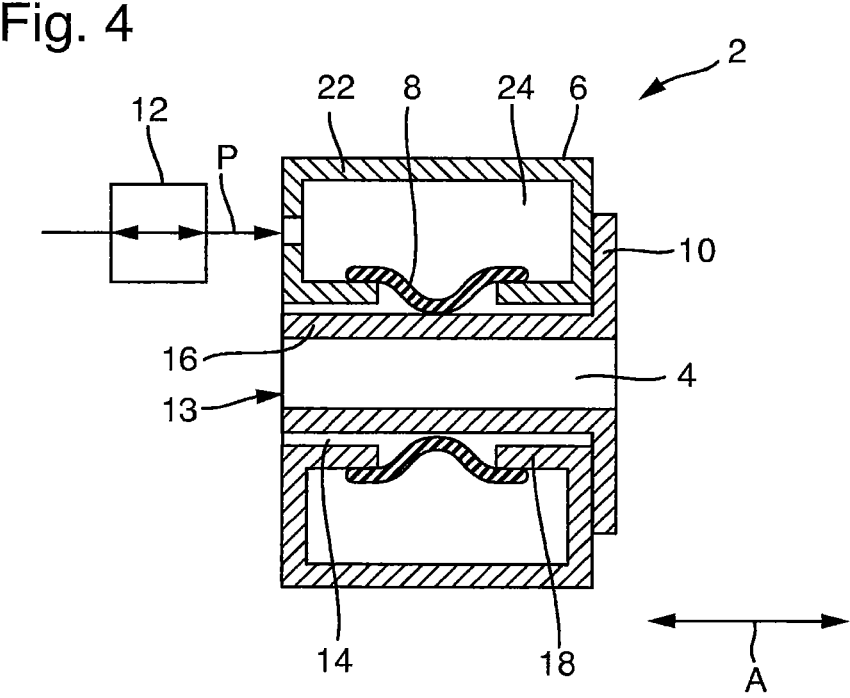

CONNECTING DEVICE, CLEANING AND/OR DISINFECTING DEVICE AND METHOD FOR THE OPERATION THEREOF

CROSS-REFERENCE TO RELATED APPLICATION

The present application is a continuation of PCT/EP2015/055692 filed on Mar. 18, 2015, which is based upon and claims the benefit to DE 10 2014 206 020.6 filed on Mar. 31, 2014, the entire contents of each of which are incorporated herein by reference.

BACKGROUND

Field

The present application relates to a connecting device for coupling a rinsing system to a surgical element channel to be cleaned, such as an endoscope channel of an endoscope, wherein the connecting device comprises a supply-side coupling apparatus having a receiving channel that is configured to receive a connecting element which extends within the holding channel in a longitudinal axial direction of the holding channel in a connected state, and which is provided at the end of a connecting channel that communicates with the channel of the surgical instrument that is to be cleaned, wherein the holding channel is connected to the rinsing system for feeding a rinsing liquid to the channel to be cleaned, wherein the coupling apparatus has a sealing element.

In addition, the present application relates to a cleaning and/or disinfecting device for cleaning and/or disinfecting surgical instruments, such as endoscopes, with a channel to be cleaned, such as for cleaning and/or disinfecting endoscopes with an endoscope channel to be cleaned, comprising a cleaning chamber in which the surgical instruments to be cleaned and/or disinfected, such as endoscopes, can be or are held during the cleaning and/or disinfecting process.

Finally, the present application relates to a method for operating such a cleaning and/or disinfecting device.

Prior Art

Stringent demands are placed on the post-usage reprocessing of endoscopes in a cleaning and disinfecting device for endoscopes, RDG-E for short, in the medical field. Reprocessing typically comprises the steps: washing, disinfecting and drying the endoscopes. One or two washing or pre-washing stages precedes disinfection. This is followed by rinsing stages with clear water and drying stages. For washing and disinfecting, one or more chemicals for disinfecting are added to the detergent and cleaning agent, respectively.

Importance can be ascribed to the cleaning and disinfection of the endoscope channels when reprocessing the endoscopes. To reprocess the endoscope, the channels are connected to the rinsing circuit of the RDG-E. Special connecting elements are used for connecting. The connection between the endoscope and connecting element is frequently done manually. However, it is desirable for the connection to occur automatically between the connecting element and reprocessing device. Depending on the type and design of the RDG-E, it is difficult, time-consuming and also error-prone to perform a manual connection to the connecting element(s).

One reprocessing device is for example known under the designation of ETD 3 by the manufacturer Olympus Medical Systems, wherein the abbreviation ETD stands for Endo Thermo Disinfector. This reprocessing device is equipped with different reprocessing programs and allows the simultaneous reprocessing of several flexible or rigid endoscopes. In the ETD machines, the connecting elements and rinsing circuit of the machine are automatically coupled.

In the ETD 3, the connecting elements which are connected to the endoscopes to be cleaned are passively coupled to the rear wall of the rinsing chamber by inserting the cleaning basket which accommodates the endoscopes to be cleaned. Alternatively, a module located on the side of the rinsing chamber is used for coupling and actively connects a connecting element plate to the ETD with the assistance of a motor.

In passive coupling methods, a mechanical resistance must be overcome since, when inserting the connecting coupling, a device-side sealing situation must be established. In addition, a lock is frequently necessary which requires the expenditure of additional force, or respectively additional steps on the part of the user. Mechanically overcoming a sealing situation further causes increased wear. In addition, the force to be applied by the user frequently at least partially affects the wall of the rinsing chamber. Especially when the thickness of the wall is minimal, this causes undesirable permanent deformations.

Active coupling methods (such as by using motors) are significantly more expensive and require significant installation space in the reprocessing device. In addition, actively driven systems frequently require much servicing.

SUMMARY

In view of the prior art, an object to be solved is to present a connecting device, a cleaning and/or disinfecting device and method for operating a cleaning and disinfecting device, wherein reliable and extremely low-wear coupling of a channel to be cleaned to a rinsing system can be provided, and wherein the construction effort can be minimized.

Such object can be achieved with a connecting device for coupling a rinsing system to a channel of a surgical instrument to be cleaned, such as an endoscope channel of an endoscope, wherein the connecting device comprises a supply-side coupling apparatus having a holding channel that is configured to receive a connecting device which extends within the holding channel in a longitudinal axial direction of the holding channel in a connected state, and which is provided at the end of a connecting channel that communicates with the channel of the surgical instrument that is to be cleaned, wherein the holding channel is connected to the rinsing system for feeding a rinsing liquid to the channel to be cleaned, wherein the coupling apparatus has a sealing element, wherein the connecting device is developed in that the sealing element is elastic and means for hydraulically and/or pneumatically actuating the sealing element are provided, wherein the hydraulically and/or pneumatically actuated sealing element reduces a cross-section of the holding channel in a region of the sealing element by means of an expansion transverse to the longitudinal axial direction such that a liquid-tight connection of the connecting element to the coupling apparatus can be or is provided.

The present disclosure makes use of the consideration that a liquid-tight connection between a coupling apparatus and a connecting element using a hydraulically and/or pneumatically actuated sealing element operates with low-wear, requires practically no additional exertion of force to couple the connecting element to the coupling apparatus, and can be realized with a simple design. The hydraulically and/or pneumatically actuatable seal guarantees a reliable liquid-tight, hygienically unobjectionable sealing situation between a connecting channel of the connecting element and the channel of the surgical instrument to be cleaned. The cleaning and/or disinfecting liquid does not come into contact with an outer chamber so that the channel to be cleaned can be reliably and hygienically rinsed.

According to one embodiment, the connecting device is enhanced in that an overpressure chamber and compressed air supply are provided, wherein the compressed air supply is connected to the overpressure chamber, and the sealing element forms at least one section of a wall of the overpressure chamber.

The sealing element is expanded when the overpressure chamber is supplied with compressed air. The overpressure chamber can be supplied with an overpressure. An overpressure designates a pressure higher than atmospheric pressure. This overpressure causes the sealing element to elastically deform and hence to expand until a reliable sealing situation is established between the coupling apparatus and the connecting element.

The sealing element can be provided as a separate component, such as a tubular seal, which can comprise a rubber elastic material such as rubber or silicone, is used whose inner chamber is the overpressure chamber. Such a tubular seal, or respectively such a sealing hose, is expanded by applying an overpressure within its interior so that its cross-section increases. This design of a connecting device can be particularly economical.

According to one embodiment, the coupling apparatus further comprises the overpressure chamber, wherein the overpressure chamber extends along an outer perimeter of the holding channel, and wherein the sealing element is a sealing membrane that limits the overpressure chamber at an inner wall of the overpressure chamber, said wall facing the holding channel.

The overpressure chamber can be integrated in the coupling apparatus, in other words, it is an integral component of the coupling apparatus.

The coupling apparatus, including the overpressure chamber, can be manufactured economically as a common component, such as in an injection molding process. The sealing element is largely protected from unintentional or accidental damage by its arrangement on the inner wall of the overpressure chamber. This increases the reliability and durability of the connecting device.

Furthermore, the connecting device can be enhanced in that the overpressure chamber passes along the entire perimeter of the holding channel, wherein by applying an overpressure to the overpressure chamber, a liquid-tight coupling of the connecting element to the coupling apparatus can be or is provided in that a sealing seat is establishable or established between the expanded sealing element that extends beyond the inner wall of the overpressure chamber and hence locally reduces the cross-section of the holding channel, and an outside of a coupling of the connecting element extending within the holding channel.

Furthermore, an outer component of the coupling apparatus can comprise an overpressure chamber connected to a compressed air supply, wherein the inner wall of the overpressure chamber is interrupted in a ring-shape along the perimeter of the holding channel such that the inner wall has an annular gap, wherein the annular gap is sealed by the elastic sealing membrane as a sealing element.

If the sealing element is expanded by pneumatic actuation, it forms a sealing seat with the outside of the coupling of the connecting element proceeding from the inner wall of the overpressure chamber.

A sealing element introduced in a partition wall between the overpressure chamber and the holding channel, such as an elastic sealing membrane, which can comprise a rubber elastic material like rubber or silicone, is largely protected from damage, even when the connecting element is inserted into the coupling apparatus. Accidental damage to the sealing element is hence practically excluded; this increases the reliability and durability of the connecting device.

Such object is further achieved by a cleaning and/or disinfecting device for cleaning and/or disinfecting surgical instruments, such as endoscopes, with a channel to be cleaned, such as an endoscope channel to be cleaned, comprising a cleaning chamber in which the surgical instruments to be cleaned and/or disinfected, such as endoscopes, can be or are held during the cleaning and/or disinfecting process, wherein the cleaning and/or disinfecting device is developed in that a connecting device is provided according to one or more of the cited embodiments that can be arranged on a wall of the cleaning chamber or inserted into a wall of the cleaning chamber.

The cleaning and/or disinfecting device can comprise a rinsing system that comprises pumps, sensors and valves in addition to a rinsing liquid reservoir that can comprise a cleaning agent and/or disinfectant for cleaning and/or disinfecting the channel to be cleaned, such as the channel of the surgical instrument, such as an endoscope.

The same or similar features as already mentioned with regard to the connecting device also apply to the cleaning and/or disinfecting device and will not be repeated.

Such object is further solved by a method for operating a cleaning and/or disinfecting device according to one or more of the cited embodiments, wherein the method comprises the steps of:

introducing a coupling of the connecting element along the longitudinal axial direction of the holding channel into the holding channel of the supply-side coupling apparatus, applying an overpressure to the sealing element by supplying hydraulic and/or pneumatic fluid under an overpressure to the sealing element to hydraulically and/or pneumatically actuate the sealing element such that the actuated sealing element reduces a cross-section of the holding channel in the region of the sealing element by an expansion transverse to the longitudinal axial direction, supplying rinsing liquid to the holding channel so that, proceeding from the holding channel through the connecting channel, the rinsing liquid is available to clean and disinfect the channel of the surgical instrument to be cleaned, such as to clean and/or disinfect an endoscope channel of an endoscope, and reducing the pressure of the hydraulic and/or pneumatic fluid in order to decrease the overpressure acting on the sealing element by the fluid such that the connecting element is released from the coupling apparatus.

The connecting element can be manually connected to the surgical instrument to be cleaned, such as to the endoscope. Furthermore, the coupling(s) of the connecting element(s) that are subsequently connected to the coupling apparatus can be releasably or permanently attached to a cleaning basket for receiving the surgical instruments. Such a cleaning basket is inserted into a cleaning chamber of the cleaning and/or disinfecting device, wherein, during this movement, the coupling of the connecting element can be inserted along the longitudinal axial direction of the holding channel into the holding channel of the supply-side coupling apparatus.

This movement occurs without having to overcome the resistance of a sealing situation. Likewise, an additional manipulation to lock the connecting element is omitted.

The coupling apparatus can be located on a rear wall of the treatment chamber. It is positioned to match the connecting elements and, can be coordinated with the guides, or respectively stops, of the cleaning basket such that, when the cleaning basket is shoved in, a coupling of the connecting element is inserted into the holding channel of the coupling apparatus.

Furthermore, a definitive stop can be provided in order to signal the user that the cleaning basket is located in the end position.

In the end position, a liquid-tight contact between the coupling apparatus and connecting element is not yet established. No significant exertion of force is required to reach the end position and establish the connection between the connecting element and coupling apparatus.

If the user subsequently closes the cleaning and/or disinfecting device and selects a corresponding cleaning and/or disinfection program, the sealing element is hydraulically and/or pneumatically actuated which expands the sealing element, such as elastically. Compressed air can be supplied to a pressure chamber.

The sealing element, or respectively the sealing membrane, deforms until a reliable sealing situation is established between an outside of the coupling, such as an outside of a coupling, and the sealing element. The channel to be cleaned of the surgical instrument, such as the endoscope channel, can now be supplied with cleaning fluid. It is rinsed with the rinsing liquid taken from the rinsing liquid reservoir. The rinsing liquid can be water and/or a cleaning and/or disinfecting solution. The water and/or the cleaning and/or disinfecting solution can be heated to or above a settable temperature.

According to another embodiment, the method can include the following additional steps:

supplying compressed air to an overpressure chamber at least partially enclosed by the sealing element, wherein a supply pressure level of the compressed air is changed by turning on or turning off a compressed air supply; and measuring a time-dependent pressure in the overpressure chamber and comparing the measured pressure with a settable target pressure, wherein by turning on or turning off the compressed air supply, the target pressure is maintained for a duration of the cleaning and/or disinfecting process.

Furthermore, the pressure can be measured in the overpressure chamber at an access to the overpressure chamber connected to a compressed air supply over a first period of time, wherein the supply pressure level is then changed in steps, and a step response of the pressure predominating in the overpressure chamber to the change in the supply pressure level is measured and analyzed, wherein the analysis provides information on a sealing of the overpressure chamber, such as a sealing of the sealing element, and/or information on a presence or absence of a coupling of the connecting element in the holding channel.

According to another embodiment, the analysis contains the formation of an integral of the measured pressure over a settable time, the determination of a rise and/or the formation of a second derivative of the pressure measured as a step response over time, wherein a comparison with a set target value is performed, and if the set target value is exceeded or undershot, an insufficient seal of the overpressure chamber, such as of the sealing element, and/or a presence or absence of the coupling of the connecting element in the holding channel is assumed.

In other words, the pressure can be maintained over the duration of the cleaning program. A slight leakage rate is compensated.

In order to detect a damaged sealing element and/or a presence or absence of the coupling of the connecting element in the holding channel, the supply pressure level is changed in steps, and a sealing of the overpressure chamber, or respectively an elastic behavior of the sealing element from a step response of the change in the supply pressure level is measured and analyzed.

The analysis can comprise a comparison of the static pressure with a first value that can be set for the overpressure chamber.

Furthermore, the analysis can comprise the formation of an integral of the measured pressure over a second settable time, and a comparison with a second value that can be set for the overpressure chamber.

In addition, the analysis can comprise the determination of a rise and/or the formation of a second derivative of the measured pressure over time.

Finally, the analysis can comprise the analysis of the duration, amplitude and/or wavelength of an oscillation of the pressure measured as a step response.

If the drop in pressure exceeds a specific threshold, this is considered an indication of a defective sealing element, wherein a corresponding error or notification signal can be emitted. In this regard, thresholds are determined, such as with reference to the formed integral over a second settable time, the formed rise and/or the second derivative of the measured pressure over time, as well as the duration, amplitude and/or wavelength of an oscillation of the pressure measured as a step response, and an excessive leakage rate is assumed when the thresholds are exceeded or undershot.

The functionality of the sealing element can therefore be reliably checked.

The presence or absence of the coupling of the connecting element in the holding channel is detected by the mechanical, or respectively elastic reaction of the sealing element to the changed internal pressure in the overpressure chamber. The sealing element manifests different elastic behavior depending on whether or not the coupling is the holding channel. The coupling can exert a corresponding counterforce on the sealing element, and furthermore limits the volume available for elastic deformation, or respectively expansion. By analyzing a rise and/or the formation of a second derivative of the measured pressure over time, it can be determined whether the coupling is located in the holding channel Furthermore, an analysis of a duration, amplitude and/or wavelength of an oscillation of the pressure measured as a step response is useful for this purpose.

After the termination of the cleaning process, the compressed air channel is ventilated which releases the connecting element from the coupling apparatus. The user is again able to remove the basket with the contained, clean surgical instruments without an exertion of force being necessary to overcome a sealing situation.

Further features will become apparent from the description of embodiments together with the claims and the included drawings. Embodiments disclosed herein can fulfill individual characteristics or a combination of several characteristics.

BRIEF DESCRIPTION OF THE DRAWINGS

The embodiments are described below without restricting the scope of the claims, using exemplary embodiments with reference to the drawings, wherein we expressly refer to the drawings with regard to all details that are not explained in greater detail in the text. In the figures:

FIGS. 1 to 4 schematically illustrate a connecting device in a view of a longitudinal section during different operating states.

In the drawings, the same or similar types of elements and/or parts are provided with the same reference numbers so that a re-introduction is omitted.

DETAILED DESCRIPTION

Figure 1:
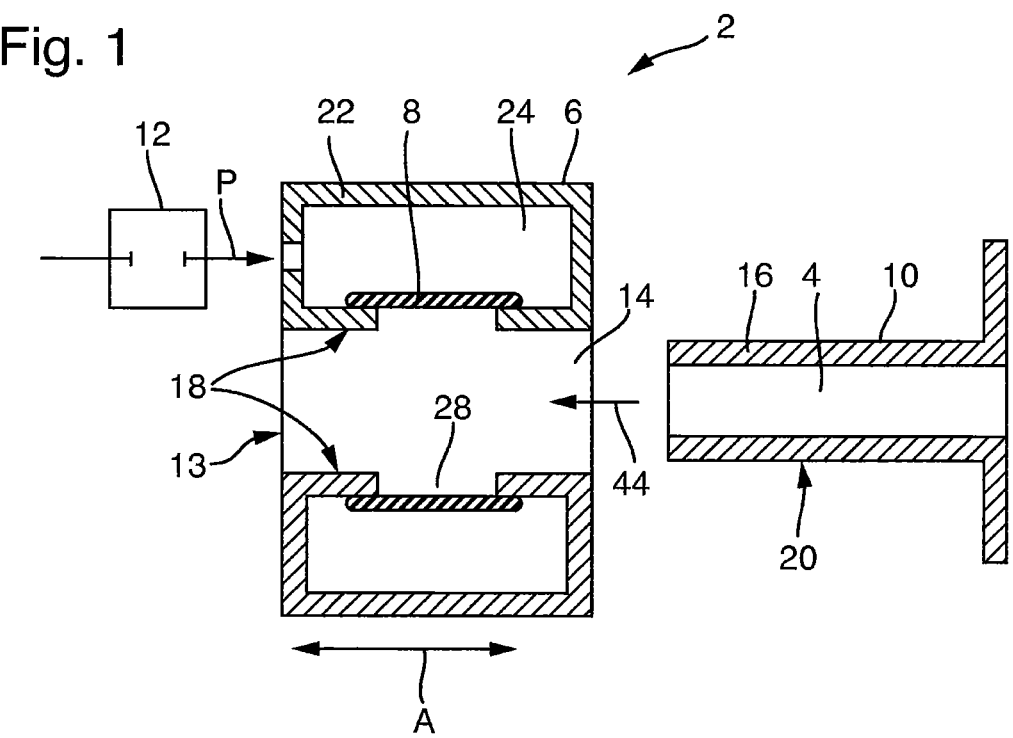

FIGS. 1 to 4 schematically illustrate a connecting device 2 in a view of a longitudinal section in different operating states. The connecting device 2 comprises a coupling apparatus 6 and a connecting element 10 that is connectable to the coupling apparatus 6. The is coupling apparatus 6 is on the supply side, and serves to provide a rinsing liquid 5 such as water or a cleaning and/or disinfecting liquid for cleaning and/or disinfecting a channel to be cleaned of a surgical instrument, such as an endoscope channel of an endoscope. To this end, the coupling apparatus 6, more precisely the holding channel 14 of the coupling apparatus 6, is connected by a supply opening 13 to a rinsing system 50. The connection channel 4 of the connecting element 10 is connected to the channel to be cleaned of the surgical instrument.

Figure 5:
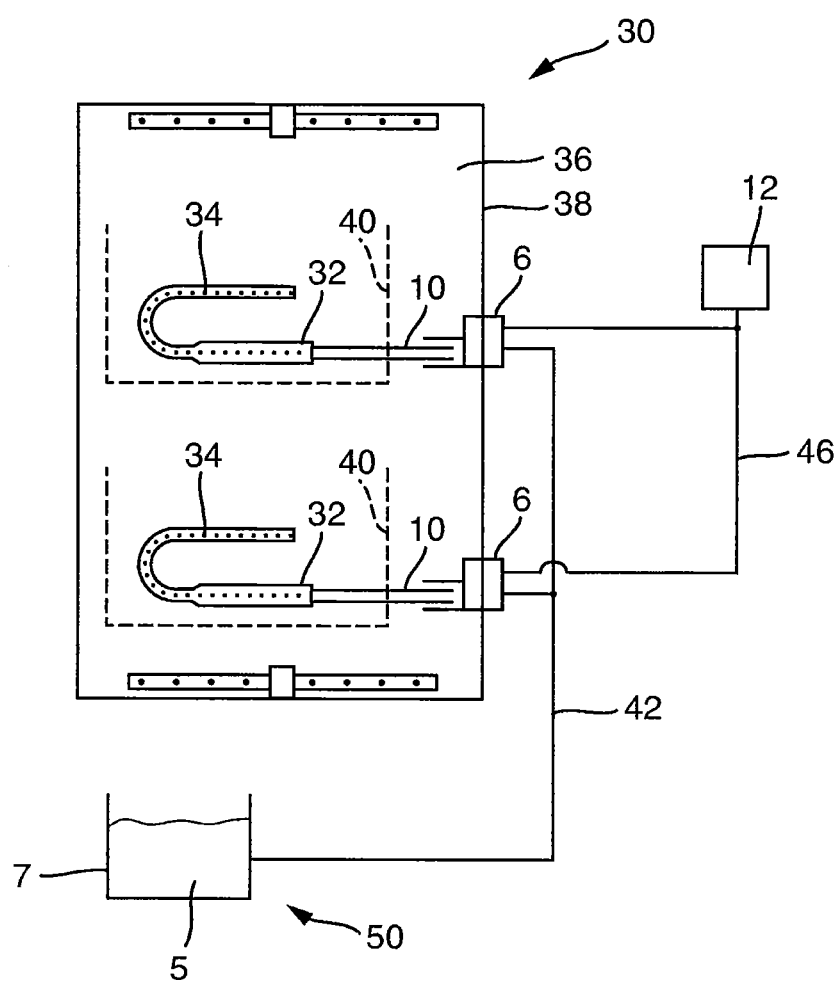
FIG. 5 illustrates a schematic cleaning and disinfection device.

FIG. 5 shows the same cleaning and disinfecting device 30 in which the coupling apparatus 6 is integrated. It can be located on a rear wall 38 of a cleaning chamber 36. The cleaning and/or disinfecting device 30 serves to clean and disinfect surgical instruments with a channel to be cleaned, such as cleaning and/or disinfecting endoscopes 32, as depicted with an endoscope channel 34 to be cleaned.

The supply opening 13 (see FIGS. 1 to 4) is connected to the rinsing liquid reservoir 7 by a supply line 42 (see FIG. 5) so that the rinsing liquid 5 can be supplied to the coupling apparatus 6 through its supply opening 13. In addition to the rinsing liquid reservoir 7, the rinsing system 50 comprises pumps, sensors and valves (not shown).

The connecting element 10 is connected to the endoscope 32 to be cleaned. The connecting channel 4 in the connecting element 10 hence communicates with an endoscope channel 34 to be cleaned. After the connection has been established between the coupling apparatus 6 and the connecting element 10, the channel is rinsed with rinsing liquid 5, such as a cleaning and/or disinfecting liquid, from the rinsing liquid reservoir 7.

At the beginning of the cleaning process, the connecting element 10 can be connected manually to the endoscope 32 to be cleaned. The coupling 16 of the connecting element that is used can be fastened releasably or permanently to a cleaning basket 40 for holding the endoscope 32.

If the user places the cleaning basket 40 including the endoscopes 32 to be cleaned into a cleaning chamber 36 of the cleaning and/or disinfecting device 30, the coupling 16 is inserted into the holding channel 14 of the coupling apparatus 6 in a connecting direction 44 during this movement. The connecting device is at least approximately parallel to a longitudinal axial direction A of the holding channel 14. The cross-section of the holding channel and the coupling 16 14 can be circular.

The coupling apparatus 6 can be located on the rear wall 38 of the treatment chamber 36. It can be positioned to match the position of the connecting element 10 on the is cleaning basket 40. The positions of the connecting element 2 on the cleaning basket 40, and the position of the coupling apparatus 6 on the rear wall 38 of the treatment chamber 36 can be coordinated with each other by the guides and stops of the cleaning basket 40 so that, when the cleaning basket 40 is inserted, the couplings 16 are inserted into the associated holding channel 14.

This movement can occur without having to overcome a resistance of a sealing situation. A diameter of the coupling 16 and a diameter of the holding channel 14 are coordinated with each other taking into account sufficient tolerances and gap dimensions.

Figure 2:
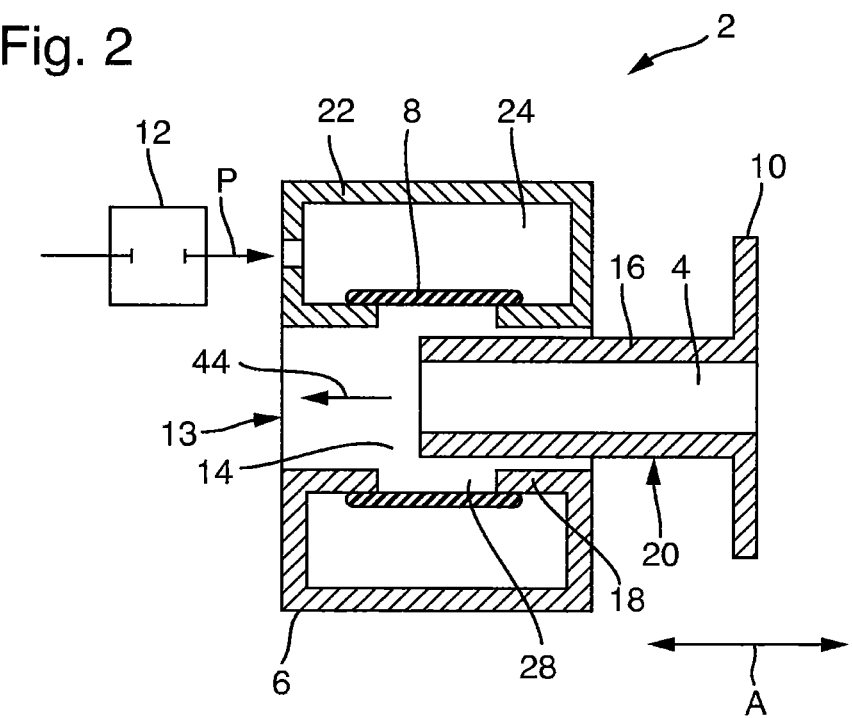

The process of inserting the coupling 16 into the holding channel 14 is depicted in FIGS. 1 to 3 during different sequential phases.

A definitive stop can be provided in order to signal to the user that the cleaning basket is located in the end position. The end position can be reached when the collar of the connecting element 10 lies against the flat side of the seat 6 facing the connecting element 10.

In the end position as shown in FIG. 3, a liquid-tight contact between the coupling apparatus and connecting element 6 is not yet established. No particular exertion of force can be required to reach the end position.

A liquid-tight connection between the connecting element 10 and coupling apparatus 6 is achieved by hydraulically and/or pneumatically actuating an elastic sealing element. According to the depicted embodiment, a sealing membrane 8 can be provided as the sealing element. In order to actuate the sealing membrane 8, an outside component 22 of the coupling apparatus 6 comprises an overpressure chamber 24 that can be supplied an overpressure with the assistance of the compressed air supply 12. To this end, the coupling apparatus 6 is connected by a compressed air line 46 to the compressed air supply 12.

The provided sealing membrane 8 is elastically deformable. If, after the end position is reached, the user then closes the cleaning and/or disinfecting device 30 and selects the corresponding cleaning and/or disinfection program, the overpressure chamber 24 is supplied with compressed air P by activation of the compressed air supply 12.

The membrane 8 is hydraulically and pneumatically actuated, wherein due to an expansion of the membrane 8 in a direction transverse to the longitudinal axial direction A, a cross-section of the holding channel 14 is reduced in the region of the membrane 8 until a liquid-tight connection of the connecting element 10 with the coupling apparatus 6 can be or is provided.

The sealing element, i.e., the sealing membrane 8, is located on, or respectively in, an inner wall 18 of the overpressure chamber 24. It is expandable upon pneumatic actuation, i.e., when an overpressure is generated in the overpressure chamber 24 so that a sealing seat can be established between the membrane 8 and the outside 20 of the coupling 16 of the connecting element 10. The outer component 22 of the coupling apparatus 6 comprises an annular gap 28 extending along the perimeter of the holding channel 14. This arises from an annular interruption of the inner wall 18 which extends between the holding channel 14 and the overpressure chamber 24. The annular gap 28 is sealed by the elastic sealing membrane 8 as the sealing element. If the overpressure chamber 24 is supplied with an overpressure, the sealing membrane 8 bulges through the annular gap 28 to establish a reliable sealing seat. This situation is schematically illustrated in FIG. 4.

According to another exemplary embodiment (not shown), an annular or tubular seal is provided that is also located on the inner wall 18 and extends completely along the inner circumference of the holding channel 14. In this exemplary embodiment, an overpressure chamber 24 in the interior of the outer component 22 can be omitted. The inner chamber of the tubular seal assumes the technical function of the overpressure chamber 24. According to this exemplary embodiment, the inner wall 18 can be provided with means for receiving and holding a tubular seal; which can have a peripheral groove. In a pressure-free state, such a tubular seal lies flat against the inside of the inner wall 18. It expands if it is supplied with pressure, such as with an increase of its circumference, so that a sealing seat is producible between the seal and an outside 20 of the coupling 16 of the connecting element 10.

After compressed air P is supplied to the overpressure chamber 24 of the coupling 16, the supply pressure level of the compressed air P is changed by turning on or off the compressed air supply 12, or respectively is maintained for the duration of the cleaning and disinfection process. To this end, the pressure in the overpressure chamber 24 is measured over time; a corresponding sensor (not shown) is provided. The desired pressure within the overpressure chamber 24 is maintained by a comparison with a predetermined reference value.

This ensures that, for the duration of the cleaning and/or disinfecting procedure, the sealing seat exists between the membrane 8 and outside 20 of the connecting element 6. After the conclusion of the cleaning and/or disinfecting procedure, the compressed air P is discharged from the overpressure chamber 24 so that the coupling apparatus 6 releases of the connecting element 10.

To detect a damaged sealing element, the cleaning and/or disinfecting device 30 can be configured to supply compressed air P to the overpressure chamber 24 at a supply pressure level, wherein the supply pressure level of the compressed air P is changed by turning on or turning off the compressed air supply 12. The pressure is measured at an inlet to the overpressure chamber 24, or in a supply line of the overpressure chamber 24, over a first settable time. The supply pressure level is then changed in steps. A seal of the overpressure chamber 24 is detected with reference to a measured step response to the change in the supply pressure level by analyzing the step response.

This analysis can comprise a comparison of the static pressure with a first value that can be set for the overpressure chamber 24. Furthermore, this analysis can comprise the formation of an integral of the measured pressure over a second settable time, and a comparison with a second value that can be set for the overpressure chamber 24. In addition, the analysis can comprise the determination of a rise and/or the formation of a second derivative of the measured pressure over time. Finally, the analysis can comprise the analysis of the duration, amplitude and/or wavelength of an oscillation of the pressure measured as a step response.

If the drop in pressure exceeds a specific threshold, this is considered an indication of a defective sealing element, such as, a defective sealing membrane 8. The cleaning and/or disinfecting device 30 can be configured to output a corresponding error or notification signal which prompts to service or exchange the sealing element.

Furthermore, it is possible to determine the presence or absence of the coupling 16 of the connecting element 10 in the holding channel 14 with reference to the elastic reaction of the sealing membrane 8. If the inner pressure of the overpressure chamber 24 changes, the sealing membrane 8 manifests a different elastic behavior depending on whether or not the coupling 16 is present in the holding channel 14.

The coupling 16 can exert a counterforce on the sealing membrane 8, and furthermore limits the volume available for elastic deformation, or respectively expansion. By analyzing a rise and/or the formation of a second derivative of the pressure measured over time, it can be determined whether the coupling 16 is located in the holding channel 14. Furthermore, an analysis of a duration, amplitude and/or wavelength of an oscillation of the pressure measured as a step response to a change in the inner pressure is useful for this purpose.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Connecting device
4 Connecting channel
5 Rinsing liquid
6 Coupling apparatus
7 Rinsing liquid reservoir
8 Sealing membrane
10 Connecting element
12 Compressed air supply
13 Supply opening
14 Holding channel
16 Coupling
18 Inner wall
20 Outside
22 Outer component
24 Overpressure chamber
26 Partition wall
28 Annular gap
30 Cleaning and/or disinfecting device
32 Endoscope
34 Endoscope channel
36 Cleaning chamber
38 Wall
40 Cleaning basket
42 Supply line
44 Connecting device
46 Compressed air lines
50 Rinsing system
P Compressed air
A Longitudinal axial direction

The invention claimed is:

1. A connecting device for coupling a rinsing system to a channel of a surgical instrument to be cleaned, the connecting device comprising:
a connecting element;
a supply-side coupling apparatus having a holding channel configured to receive the connecting element which extends within the holding channel in a longitudinal axial direction of the holding channel in a connected state, and which is provided at an end of a connecting channel that communicates with the channel of the surgical instrument that is to be cleaned, wherein the holding channel is connected to the rinsing system for feeding a rinsing liquid to the channel to be cleaned, wherein the supply-side coupling apparatus comprises a sealing element; and
means for hydraulically and/or pneumatically actuating the sealing element;
wherein the sealing element is elastic; and the hydraulically and/or pneumatically actuated sealing element reduces a cross-section of the holding channel in a region of the sealing element by means of an expansion transverse to the longitudinal axial direction to provide a liquid-tight connection of the connecting element to the supply-side coupling apparatus;

wherein the means for hydraulically and/or pneumatically actuating the sealing element comprises:

the supply-side coupling apparatus having an overpressure chamber; and a compressed air supply, wherein the compressed air supply is connected to the overpressure chamber, and the sealing element forms at least one section of a wall of the overpressure chamber.

2. The connecting device according to claim 1, wherein the supply-side coupling apparatus comprises the overpressure chamber, the overpressure chamber extends along an outer perimeter of the holding channel, and the sealing element is a sealing membrane that limits the overpressure chamber at an inner wall of the overpressure chamber, the inner wall facing the holding channel.

3. The connecting device according to claim 2, wherein the overpressure chamber passes along an entire perimeter of the holding channel, wherein by applying an overpressure to the overpressure chamber, a liquid-tight coupling of the connecting element to the coupling apparatus is provided in that a sealing seat is established between the expanded sealing element that extends beyond the inner wall of the overpressure chamber and locally reduces the cross-section of the holding channel, and an outside of a coupling of the connecting element extending within the holding channel.

4. The connecting device according to claim 2, wherein an outer component of the supply-side coupling apparatus comprises an overpressure chamber connected to a compressed air supply, the inner wall of the overpressure chamber is interrupted in a ring-shape along the perimeter of the holding channel such that the inner wall has an annular gap, and the annular gap is sealed by the elastic sealing membrane.

5. A cleaning and/or disinfecting device for cleaning and/or disinfecting a surgical instrument with a channel to be cleaned, the cleaning and/or disinfecting device comprising:

a cleaning chamber in which the surgical instrument to be cleaned and/or disinfected is held during a cleaning and/or disinfecting process; and the connecting device of claim 1 one of arranged on a wall of the cleaning chamber or inserted into the wall of the cleaning chamber.

6. A method for operating the cleaning and/or disinfecting device according to claim 5, the method comprising:

introducing a coupling of the connecting element along the longitudinal axial direction of the holding channel and into the holding channel of the supply-side coupling apparatus;

applying an overpressure to the sealing element by supplying hydraulic and/or pneumatic fluid under an overpressure to the sealing element to hydraulically and/or pneumatically actuate the sealing element such that the actuated sealing element reduces a cross-section of the holding channel in the region of the sealing element by the expansion transverse to the longitudinal axial direction, supplying rinsing liquid to the holding channel so that, proceeding from the holding channel through the connecting channel, the rinsing liquid cleans and disinfects the channel of the surgical instrument to be cleaned; and reducing a pressure of the hydraulic and/or pneumatic fluid in order to decrease the overpressure acting on the sealing element by the fluid such that the connecting element is released from the coupling apparatus.

7. The method according to claim 6, further comprising:

supplying compressed air to an overpressure chamber at least partially enclosed by the sealing element, wherein a supply pressure level of the compressed air is changed by turning on or turning off a compressed air supply; and measuring a time-dependent pressure in the overpressure chamber and comparing the measured pressure with a settable target pressure, wherein by turning on or turning off the compressed air supply, a target pressure is maintained for a duration of a cleaning and/or disinfecting process.

8. The method according to claim 6, wherein the pressure is measured in the overpressure chamber at an access to the overpressure chamber connected to a compressed air supply over a first period of time, wherein the supply pressure level is then changed in steps, and a step response of the pressure predominating in the overpressure chamber to the change in the supply pressure level is measured and analyzed, wherein the analysis provides information on a sealing of the overpressure chamber.

9. The method according to claim 8, wherein the information on the sealing of the overpressure chamber comprises one or more of information on a sealing of the sealing element or information on a presence or absence of the coupling of the connecting element in the holding channel.

10. The method according to claim 8, wherein the analysis contains the formation of an integral of the measured pressure over a settable time, the determination of a rise and/or the formation of a second derivative of the pressure measured as a step response over time, wherein a comparison with a set target value is performed, and if the set target value is exceeded or undershot, one or more of an insufficient seal of the overpressure chamber and/or a presence or absence of the coupling of the connecting element in the holding channel is assumed.

* * * * *